US006760469B1

(12) United States Patent
Berestov et al.

(10) Patent No.: US 6,760,469 B1
(45) Date of Patent: Jul. 6, 2004

(54) FLIPPING STEREOSCOPIC RADIOGRAPHS (75) Inventors: Alexander Berestov, San Jose, CA (US); Harry T. Garland, Los Altos Hills, CA (US); Roger D. Melen, Los Altos Hills, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 636 days.

(21) Appl. No.: 09/685,017

(22) Filed: Oct. 5, 2000

(51) Int. Cl.[7] .............................. G06K 9/00; A61B 6/02; G03C 9/00; G21K 4/00
(52) U.S. Cl. .......................... 382/132; 382/154; 378/41
(58) Field of Search ................................. 382/132, 154; 378/41

(56) References Cited

U.S. PATENT DOCUMENTS

| | | | | |
|---|---|---|---|---|
| 5,321,447 A | * | 6/1994 | Sander et al. | 351/216 |
| 6,108,005 A | * | 8/2000 | Starks et al. | 345/419 |
| 6,181,768 B1 | * | 1/2001 | Berliner | 378/41 |
| 6,381,302 B1 | * | 4/2002 | Berestov | 378/41 |
| 6,496,598 B1 | * | 12/2002 | Harman | 382/154 |

OTHER PUBLICATIONS

Talukdar, A. et al., Modeling and Optimization of Rotational C–Arm Stereoscopic X–Ray Angiography, *IEEE Transactions on Medical Imaging*, vol. 18, No. 7, pp. 604–616 (Jul. 1999).

Woods, A. et al., Image Distortions in Stereoscopic Video Systems, *SPIE*, vol. 1915 Stereoscopic Displays and Applications IV, pp. 36–48 (1993).

* cited by examiner

*Primary Examiner*—Leo Boudreau
*Assistant Examiner*—Hussein Akhavannik
(74) *Attorney, Agent, or Firm*—Fitzpatrick, Cella, Harper & Scinto (57) ABSTRACT

A radiographic imaging system (100) comprises an X-ray tube (110), a sensor plate (120), and a graphics engine (130). The tube (110) and the sensor plate (120) rotate synchronously about a patient (150) and expose a stereoscopic pair of images which are transmitted to the graphics engine (130). The graphics engine (130) determines (312) the geometry of the system (100). If (314) the pair of images are toed-in relative to each other, the graphics engine (130) converts (316) the images into a parallel geometry. Likewise, the graphics engine (130) also processes (320) the images for keystone distortion, if necessary. Simply flipping the images in the stereo pair distorts the depth of objects in the stereoscopic image. Instead of simply flipping the images, it is desirable to "go behind" the screen (412A) and look at the image from the back. In order to produce a stereoscopic image having this viewpoint, the graphics engine (130) uses the geometry of the radiographic system (100) to adjust (324) the screen parallax of the image after the constituent images are flipped (322) and provide the desired three-dimensional perspective.

21 Claims, 5 Drawing Sheets

FLIPPING STEREOSCOPIC RADIOGRAPHS

CROSS-REFERENCE TO RELATED APPLICATIONS

The subject matter of this application is related to the subject matter of commonly-owned U.S. patent application Ser. No. 09/428,867, filed Oct. 27, 1999, now U.S. Pat. No. 6,317,481, and commonly-owned U.S. patent application Ser. No. 09/610,579, filed Jul. 5, 2000, now U.S. Pat. No. 6,381,302, the contents of which are incorporated by reference as if fully disclosed herein.

BACKGROUND

1. Field of the Invention

This invention pertains in general to three-dimensional imaging and analysis. More specifically, the invention pertains to performing image processing on stereoscopic radiographs.

2. Background Art

Stereoscopic radiography is an effective method for obtaining three-dimensional (3-D) spatial information from two-dimensional (2-D) projection X-ray images without the need for tomographic reconstruction. In stereoscopic radiography, pairs of X-ray images of a subject exposed from slightly different positions are viewed as a 3-D image. The images can be viewed in 3-D by, for example, combining the pair of images into an anaglyph image or by rapidly alternating display of the images on a computer screen. To these ends, U.S. patent application Ser. No. 09/428,867, filed Oct. 27, 1999, now U.S. Pat. No. 6,317,481, entitled "Stereo X-ray Image Processing," describes a technique for converting pairs of 2-D X-ray images into 3-D stereoscopic radiographs. Similarly, U.S. patent application Ser. No. 09/610,579, filed Jul. 5, 2000, now U.S. Pat. No. 6,317,481, entitled "Computer Assisted 2D Adjustment of Stereo X-Ray Images," describes a technique for adjusting stereoscopic radiographs to correct for some vertical and/or horizontal distortions.

Alternatives to stereo radiography include magnetic resonance imaging (MRI), computed tomography (CT), and tomosynthetic reconstruction (TR). The first two of these techniques require expensive equipment and are very time consuming. The third technique produces images containing many artifacts, requires multiple images, and is also time consuming. Therefore, these alternatives are not as desirable as stereo radiography.

In chest radiography, radiologists, or other persons studying a radiographic image, strongly prefer to observe an image with the heart located at the right side of the image (i.e., as if the radiologist is looking at the subject from the front). This preference holds true even if the radiograph was taken from the back of the subject. A radiologist can easily manipulate a 2-D radiograph with the heart on the wrong side, such as a radiograph taken from the back of the subject, into the desired orientation by flipping the radiograph about its vertical axis.

However, such manipulations cannot be performed easily on stereoscopic radiographs. Simply flipping the original left and right images of the stereo pair distorts the 3-D effect by changing the apparent depth of the objects in the resulting stereoscopic image. Thus, the flipped 3-D image is generally unusable by a radiologist.

Therefore, there is a need in the art for a way to manipulate stereoscopic radiographs so that the radiographs can be placed in a desired orientation. The solution to this need will preferably allow a stereoscopic radiograph to be flipped about its vertical axis without introducing undesired distortions.

DISCLOSURE OF INVENTION

The above needs are met by a method, computer-readable medium, and graphics engine (130) for manipulating stereoscopic radiographs. A radiographic imaging system (100), such as an X-ray system, comprises an X-ray tube (110) (also referred to as a "camera"), a sensor plate (120), and a graphics engine (130). The tube (110) and the sensor plate (120) preferably rotate synchronously about the patient (or another subject or object being X-rayed).

In use, the sensor plate (120) and tube (110) are placed in the desired alignment relative to the patient. Then, at least two radiographic images of the patient are exposed from slightly different positions on the arc formed by rotating the sensor plate (120) and tube (110) system about the patient, or from other positions if the geometry of the system is different. The exposed images are either transmitted directly to the graphics engine (130), if a digital sensor plate is used, or converted into a digital format and then transmitted to the graphics engine.

The graphics engine (130) determines (312) the geometry of the radiographic system (100). In many instances, the geometry of the system (100) is known. If the geometry of the radiographic system (100) is unknown, however, the graphics engine (130) preferably recovers the geometry from the images. One embodiment of the present invention uses physical pointers, such as steel balls, placed around or inside the patient when the radiographic images are initially exposed in order to enable the graphics engine (130) to recover the system (100) geometry from the images.

If (314) the radiographic system has a C-arm (140) configuration, then the images in the stereoscopic pair are toed-in relative to each other. The toed-in nature of the images results in a curvature of the depth plane when the images are used as a stereo pair. Accordingly, the graphics engine (130) preferably converts (316) the toed-in images into a parallel geometry. This conversion places the images in the same plane, which is parallel to a base line between the two locations used to capture the image. The graphics engine (130) also preferably processes (320) the images to eliminate keystone distortion and moves (321) the images together in virtual space to define a screen parallax for the image. The "screen parallax" is the distance between two homologous points when the image is displayed on a screen. The amount of screen parallax determines the amount of depth in the 3-D image.

Assume that a radiologist desires to flip a stereoscopic image about its vertical axis. Simply flipping the images in the stereo pair distorts the depth of the objects in the resulting stereoscopic image. Instead of simply flipping the images, it is desirable to "go behind" the screen (412A) and look at the image from the back. In order to produce a stereoscopic image having this viewpoint, the graphics engine (130) preferably flips (322) the constituent images about the vertical axes and adjusts (324) the screen parallax of the resulting stereoscopic image. The graphics engine (130) preferably determines the proper screen parallax for the flipped image from the geometry of the radiographic system (100). An alternative embodiment of the present invention determines an area of interest in the unflipped stereoscopic image and adjusts (324) the screen parallax so that the area of interest is displayed at the level of the screen (312A) when the images are flipped.

DETAILED DESCRIPTION OF THE PREFERRED EMBODIMENTS

Figure 1:
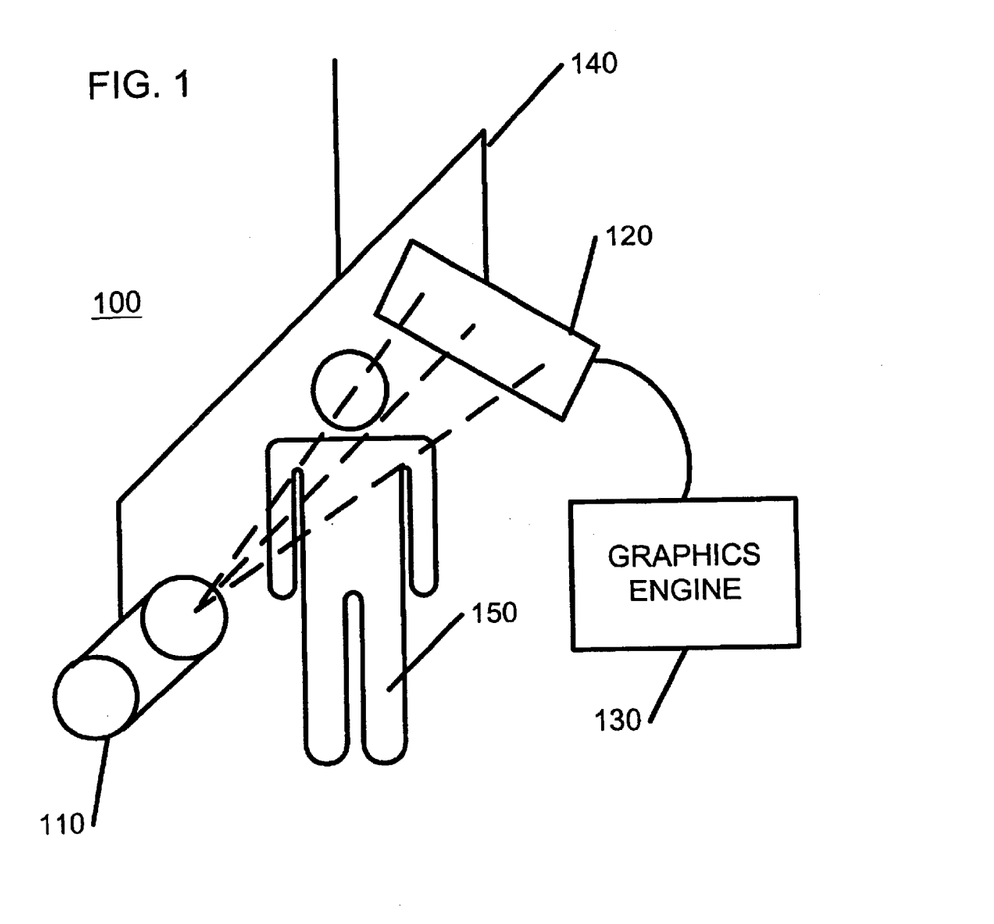
FIG. 1 is a diagram illustrating a stereoscopic radiographic imaging system for capturing three-dimensional (3-D) images.

FIG. 1 is a diagram illustrating a radiographic imaging system 100. In the illustrated embodiment, the radiographic imaging system is an X-ray system, although the present invention works equally well with other imaging systems. The imaging system 100 comprises an X-ray tube 110 (also referred to as a "camera"), a sensor plate 120, and a graphics engine 130. The tube 110 and the sensor plate 120 are mounted on a C-arm 140 and rotate synchronously about a patient 150 (or another subject or object being X-rayed). The tube 110 produces and emits X-rays that pass through the patient 150 to create varying impressions on the sensor plate 120. The sensor plate 120 comprises regular X-ray film, a digital sensor plate, or any other media that can be used to capture X-ray images.

In use, the sensor plate 120 and tube 110 are placed in the desired alignment relative to the patient 150. Then, a series of radiographic images of the patient 150 are exposed from different positions. The positions from where the images are exposed depend on the geometry of the radiographic system 100. If the system 100 uses a C-arm 140 geometry, then the images are preferably exposed from positions on the arc formed by rotating the sensor plate 120 and tube 110 about the patient. In systems having alternative geometries, such as geometries where the tube 110 and/or sensor plate 120 move in parallel or remain stationary, the positions from where the images are exposed vary accordingly. While it is possible to keep the tube 110 and sensor plate 120 stationary and move the patient 150, in most medical applications it is preferable to keep the patient immobile.

The exposed images are either transmitted directly to the graphics engine 130, if the digital sensor plate is used, or converted into a digital format and then transmitted to the graphics engine. If the radiographic images are not captured digitally, an additional digital capture device, such as a computer scanner, may be used to place the analog or film-based images into a digital format.

The digital radiographic images can be transmitted to the graphics engine 130 using, for example, a computer network, a direct link between the image capture device and the engine, and/or storage and retrieval from a digital recording medium, such as a floppy disk, compact disk, or DVD. Other means for transmitting information to the engine 130 are also available as are known to those skilled in the art.

Figure 2:
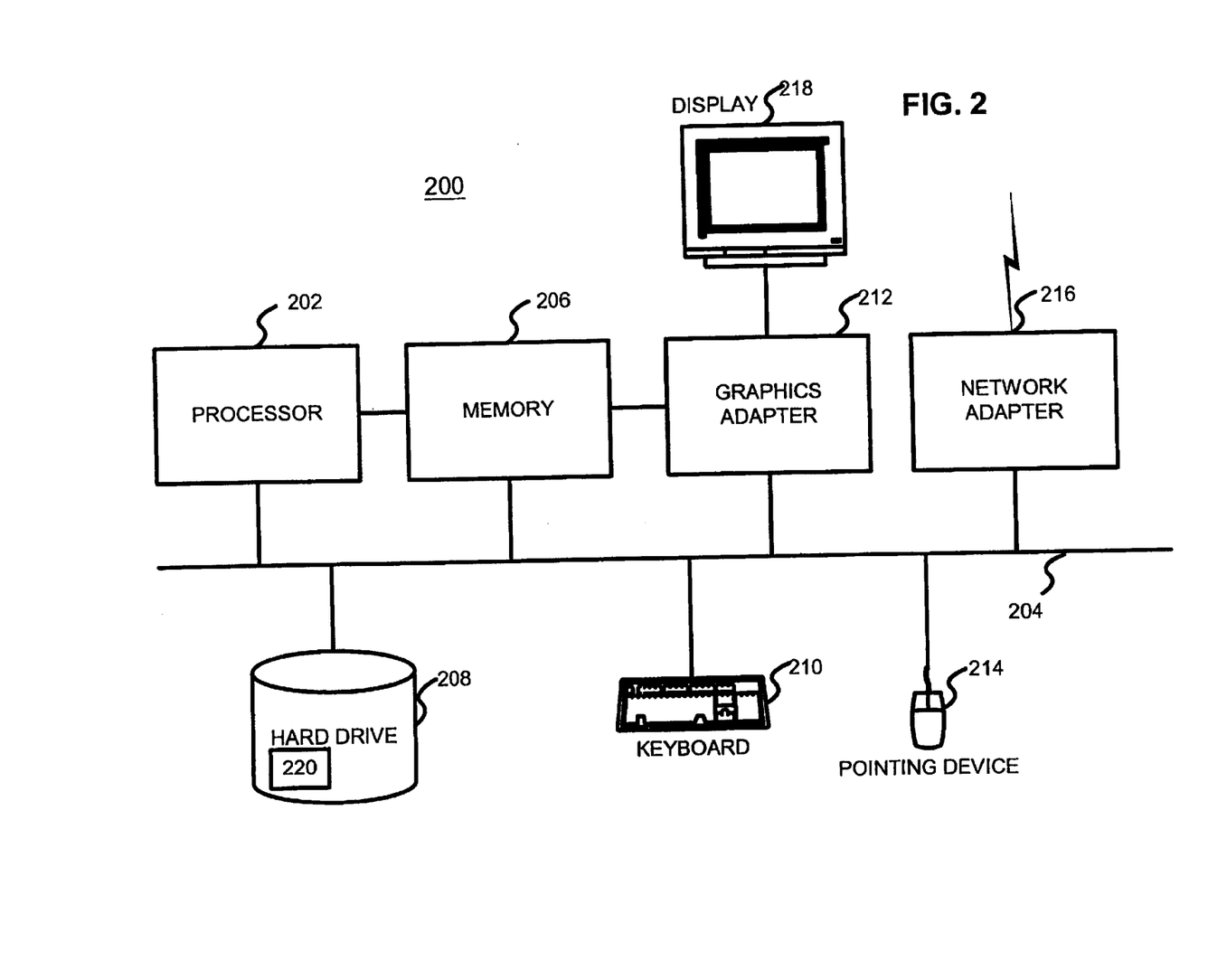
FIG. 2 is a high-level block diagram illustrating a graphics engine 130.

FIG. 2 is a high-level block diagram illustrating the graphics engine 130 in additional detail. Illustrated are at least one processor 202 coupled to a bus 204. Also coupled to the bus 204 are a memory 206, a storage device 208, a keyboard 210, a graphics adapter 212, a pointing device 214, and a network adapter 216. A display 218 is coupled to the graphics adapter 112.

The at least one processor 202 may be any general-purpose processor such as an INTEL x86, POWERPC, or MIPS-compatible central processing unit (CPU) or a dedicated processor. The storage device 208 may be any device capable of holding large amounts of data, like a hard drive, compact disk read-only memory (CD-ROM), DVD, or some other form of fixed or removable storage device. The memory 206 holds instructions and data used by the processor 202. The graphics adapter 212 displays radiographic images and other data on the display 218. The pointing device 214 may be a mouse, track ball, light pen, touch-sensitive display, or other type of pointing device and is used in combination with the keyboard 210 to input data to the graphics engine 130. The network adapter 216 optionally couples the graphics engine 130 to a local or wide area network.

Program modules 220 for providing the graphics engine 130 with the functionality described herein are preferably stored on the storage device 208, loaded into the memory 206, and executed by the processor 202. Likewise, digital radiographic images are preferably stored on the storage device 208, loaded into the memory 206, and displayed on the display 218. Alternatively, hardware and/or software modules representing programs, data, and/or functionality may be stored elsewhere within the graphics engine 130.

Figure 3:
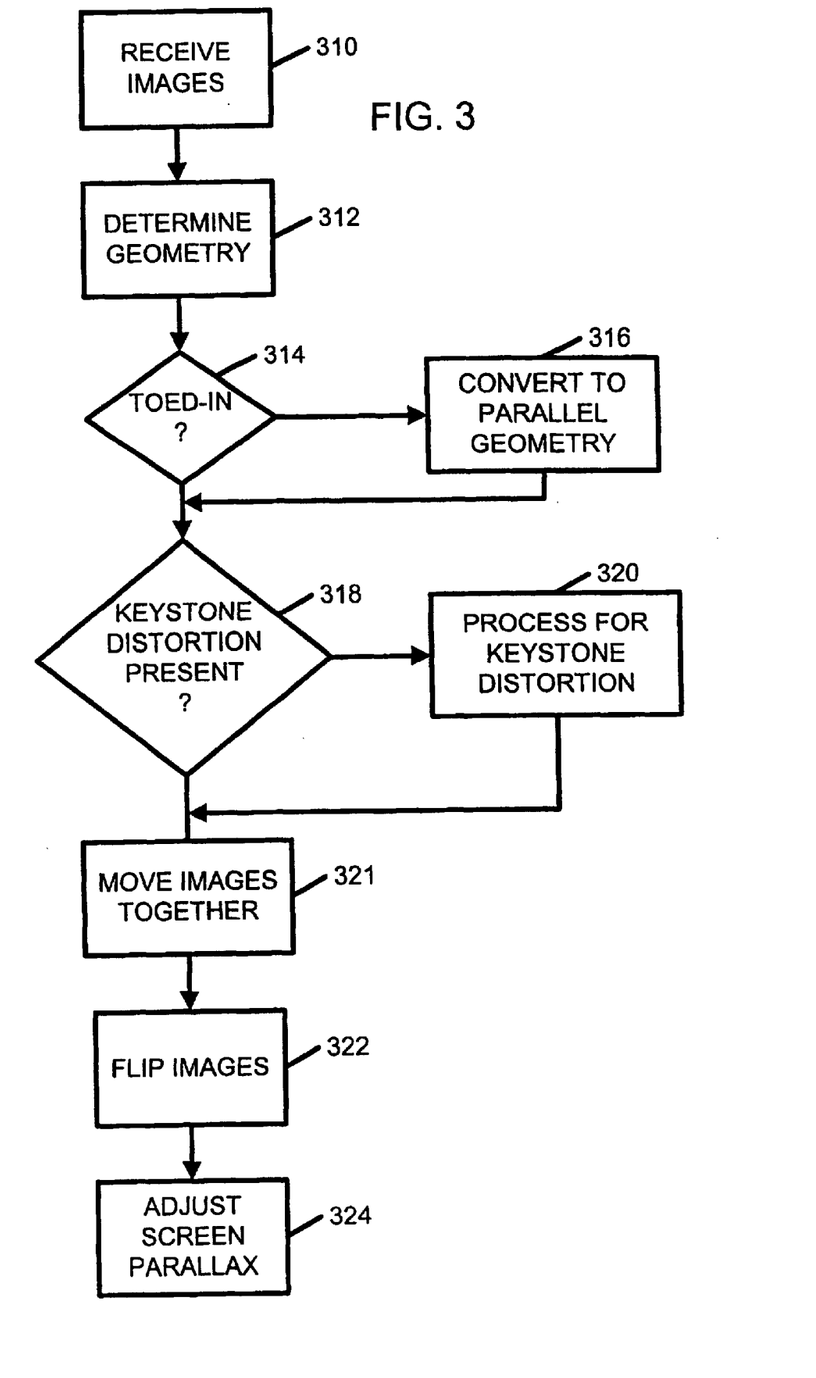
FIG. 3 is a flow chart of illustrating steps performed by the graphics engine 130 when manipulating radiographic images according to an embodiment of the present invention.

FIG. 3 is a flow chart illustrating steps performed by the graphics engine 130 when manipulating radiographic images according to an embodiment of the present invention. Initially, the graphics engine 130 receives 310 and stores a stereoscopic pair of images captured by the radiographic system 100. Next, the graphics engine preferably determines 312 the geometry of the radiographic system 100. In many instances, the geometry of the radiographic system 100 is known to the graphics engine 130. If the geometry of the radiographic system 100 is unknown, however, the graphics engine 130 preferably recovers 312 the geometry from the images. To recover the geometry, one embodiment of the present invention uses physical pointers, such as steel balls, placed around or inside the patient when the radiographic images are initially exposed. These physical pointers make distinct marks in the images. Since the real-world locations of the physical pointers are known, the marks in the images can be used to extrapolate the system geometry. Additional details of using the physical pointers to recover the system geometry are described in U.S. patent application Ser. No. 09/610,579 (now U.S. Pat. No. 6,381,302).

Once the geometry is known, the graphics engine 130 determines 314 whether the images were exposed using a toed-in, parallel, or other geometry. If, for example, the radiographic system 100 has a C-arm 140 configuration or the patient 150 was rotated between image exposures, then the images in the pair are toed-in relative to each other. If toed-in images are used as a stereo pair, the depth plane in the resulting stereoscopic image is curved. This curvature can lead to incorrectly perceived relative object distances. Accordingly, a preferred embodiment of the present invention eliminates this curvature by converting 316 toed-in images to a parallel geometry.

In order to make 316 the images parallel, the graphics engine 130 preferably rotates the first image clockwise for $\alpha/2$ and rotates the second image counter-clockwise for $\alpha/2$, where α is defined as the angle of rotation between the locations from where the first and second images were exposed. This transformation places the images in the same plane, which is parallel to a base line between the two locations from where the images were exposed.

During this transformation, the points in the images are recalculated by the engine 130 to points along the new plane. If the patient 150 is located at the center of the axis of rotation of the C-arm 140 or if the X-ray system 100 is fixed and the patient 150 rotates about the patient's vertical axis, then the coordinate x of a point in the old image, which goes into the $y^{th}$ pixel in the rotated image, is calculated using the following equation:

$$x_{r,l} = \frac{w}{2} \pm \frac{dw}{g} \frac{y_{r,l}\cos\frac{\alpha}{2}}{\frac{dw}{g} \pm y_{r,l}\sin\frac{\alpha}{2}},$$

where w is the width of the image in pixels, d is the focal length of the camera 120, g is the width of the sensor plate 120 in pixels, and r and l refer to the right and left images of the stereo pair, respectively. This transformation converts the images into a parallel geometry and eliminates the depth plane curvature. If the patient 150 is not located at the axis of rotation of the X-ray system 100, or the X-ray system does not rotate about the patient's vertical axis, then other equations are used to perform this transformation as are known in the art. Likewise, other equations are used if the movement of the tube 110 is not parallel to the movement of the sensor plate 120.

In addition, the images may 318 suffer from keystone distortion. Keystone distortion is caused by the images being exposed in different planes and causes vertical parallax in the stereoscopic image. If necessary, the graphics engine 130 preferably processes 320 the images for keystone distortion by performing epipolar line-to-line adjustment on the images. This processing also reduces errors introduced if the axis of the object rotation is not perfectly vertical. Additional details on processing for keystone distortion are found in U.S. patent application Ser. No. 09/428,867 (now U.S. Pat. No. 6,317,481).

Next, the engine 130 preferably moves 321 the images toward each other on the display screen for $$M\frac{dw}{g}\sin\frac{\alpha}{2}$$

pixels, where M is the ratio of display area width to display width in pixels, d is the focal length of the camera, w is the width of the image in pixels, g is the width of the sensor plate in pixels, and α is the angle of rotation between the images. This step 321 places the X-ray tube 110 exactly over the middle of the stereographic image and defines a screen parallax for the image. The "screen parallax" is the distance between two homologous points when the image is displayed on a screen. The amount of screen parallax between two points determines the depth of the corresponding single stereoscopic point in the 3-D image.

Figure 4:
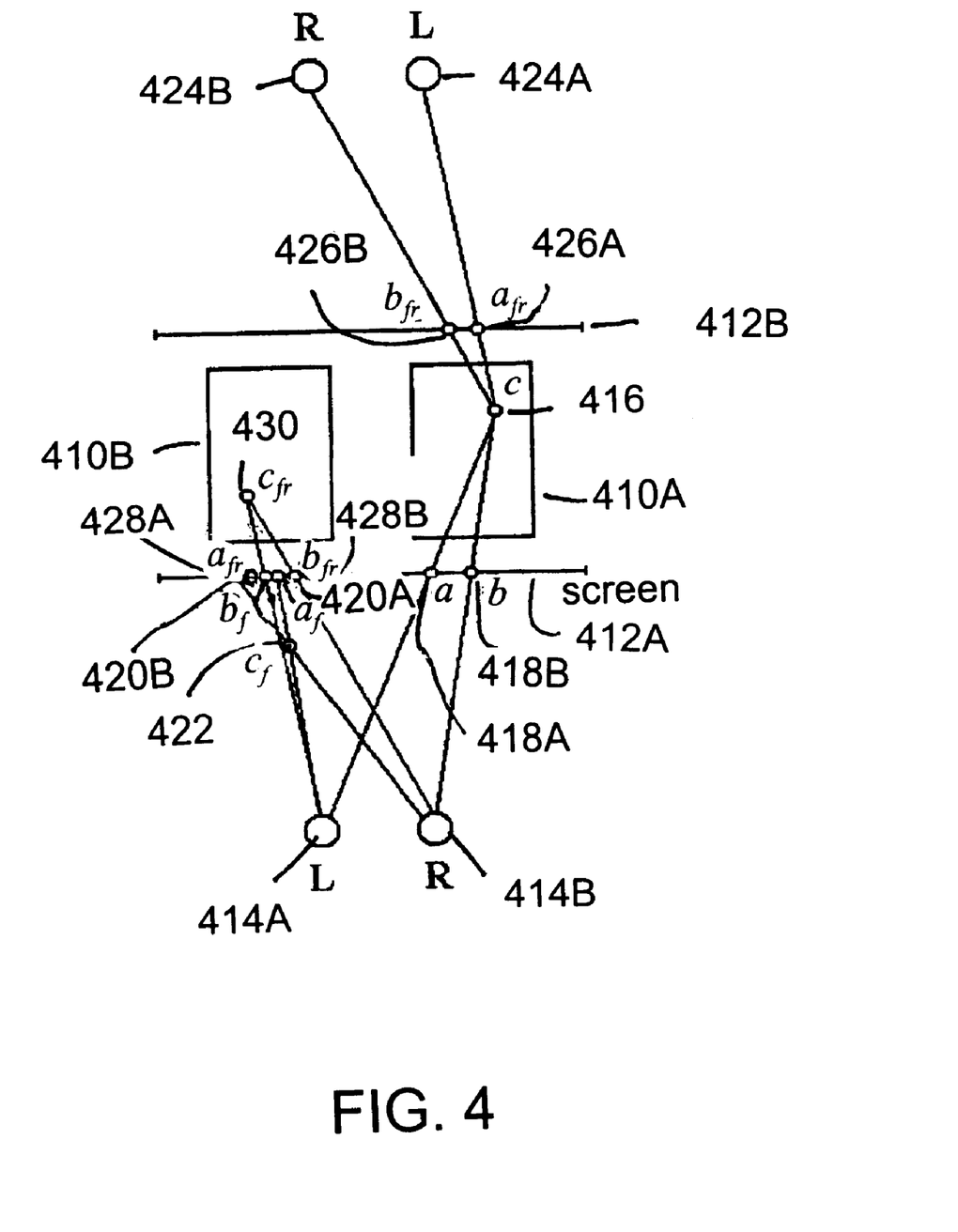
FIG. 4 is a diagram illustrating why simply flipping the images in a stereo pair introduces errors in the resulting stereoscopic image.

Assume that a radiologist desires to flip a stereoscopic image about its vertical axis. FIG. 4 is a diagram illustrating why simply flipping the images of the constituent stereo pair introduces errors into the resulting flipped stereographic image.

FIG. 4 illustrates exemplary normal 410A and flipped 410B stereoscopic images. Each image 410A, 410B can be, for example, an anaglyph or a logical stereoscopic image formed by rapidly alternating between left and right images in a pair. The images are displayed on a screen 412, such as the screen of the computer display 218. Assume a radiologist is examining the images and that the radiologist's left eye is at point 414A (also labeled 'L') and right eye is at point 414B (also labeled 'R'). In order for object c 416 to appear in 3-D "behind" the screen 412A, the left eye 414A must see the image of c at point a 418A on the screen and the right eye R 414B must see the image of c at point b 418B on the screen.

Simply flipping the image 410B about its Y axis puts points a 418A and b 418B at new locations $a_f$ 420A and $b_f$ 420B on the screen 412A. These new locations cause object c 416 to appear at location $c_f$ 422, which is in front of the screen 412A instead of behind it. However, the human brain typically has an easier time perceiving an image as being behind the screen 412A than as being in front of the screen. Therefore, the radiologist may find that the 3-D aspects of the flipped image are not readily discernable and may additionally find it difficult to view the image. Moreover, simply flipping the images may introduce other distortions into the resulting stereoscopic image.

Instead of simply flipping the images, it is desirable to "go behind" the screen 412A and look at the image from the back. In FIG. 4, this perspective is illustrated by the second pair of eyes 424A, 424B looking at the image 410A from "behind." From this perspective, the left 424A and right 424B eyes see object c 416 at points $a_{fr}$ 426A and $b_{fr}$ 426B on the screen 412B, respectively. Object c 416 is still behind the screen 412B, but is closer to the foreground than it is when viewed from the front perspective. In order to make $c_{fr}$ 430 appear in the proper position in the flipped image 410B, $a_{fr}$ and $b_{fr}$ must be located at positions 428A and 428B, respectively, on the front screen 412A.

Returning to FIG. 3, the graphics engine 130 preferably achieves this alignment by flipping 322 the images of the stereo pair about the images' vertical axes. Next, the graphics engine 130 preferably adjusts 324 the screen parallax of the stereoscopic image to make the flipped stereoscopic image equivalent to viewing the original, non-flipped stereoscopic image from behind. In the example of FIG. 4, this step 324 adjusts the screen parallax so that points $a_{fr}$ and $b_{fr}$ are located at positions 428A and 428B, respectively.

The proper screen parallax for the flipped stereoscopic image is preferably estimated from the previously-determined geometry of the radiographic system 100. For example, if the embodiment used pointers in the captured radiographic images, the present invention preferably uses those pointers as references when adjusting the screen parallax.

An alternative embodiment of the present invention determines an area of interest in the stereoscopic image and adjusts the screen parallax so that the area of interest is displayed at the level of the screen 412A, or at another depth, when the image is flipped. For example, the present invention can adjust the screen parallax of the flipped image to place one or more of the physical pointers at the level of the screen 412A. In another example of this latter embodiment, the radiologist views the stereoscopic images in normal orientation and uses the pointing device 214 to select an area of interest. Then, after the image is flipped, the graphics engine 130 adjusts 324 the screen parallax so that the region of interest is displayed at the level of the screen 412A or at another depth. This technique ensures that the flipped image displays the area of interest at a depth that is easily perceived by the radiologist.

Figure 5A:
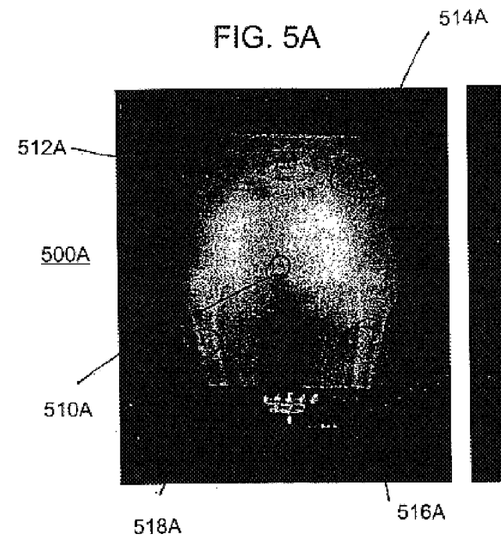
FIGS. 5A, 5B, and 5C illustrate three exemplary anaglyph images of a patient's pelvis.

FIG. 5 illustrates several exemplary anaglyph radiographic images of a patient's pelvis. FIG. 5A shows an anaglyph image 500A having five visible metal pointers: one 510A in the middle, one 512A in the top-left corner, one 514A in the top-right corner, one 516A in the bottom-right corner, and one 518A in the bottom-left corner. The pointer in the middle 510A is at the depth of the screen and appears as a single point. The other pointers are behind the screen and appear as pairs of points due to the anaglyphic nature of the image 500A.

Figure 5B:
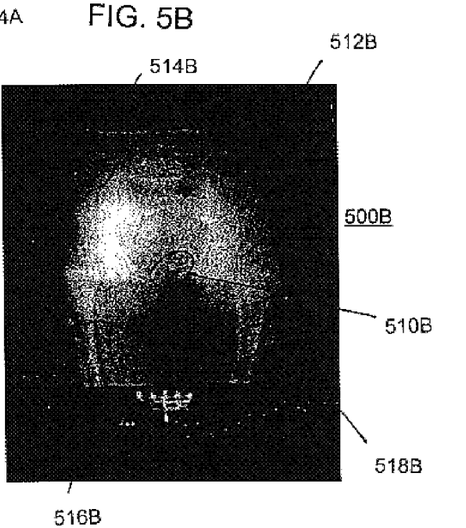

FIG. 5B shows the image 500B of FIG. 5A after the image has been flipped about its vertical axis. In FIG. 5B, the middle pointer 510B remains as a single point but has been reflected across the vertical axis of the image. Likewise, the corner pointers remain as pairs of points. Although it is difficult to notice in the image 500B, the left and right component of each pair are reversed. Thus, points that were perceived in the image 500A of FIG. 5A as being behind the screen are perceived as being in front of the screen in image 500B.

Figure 5C:
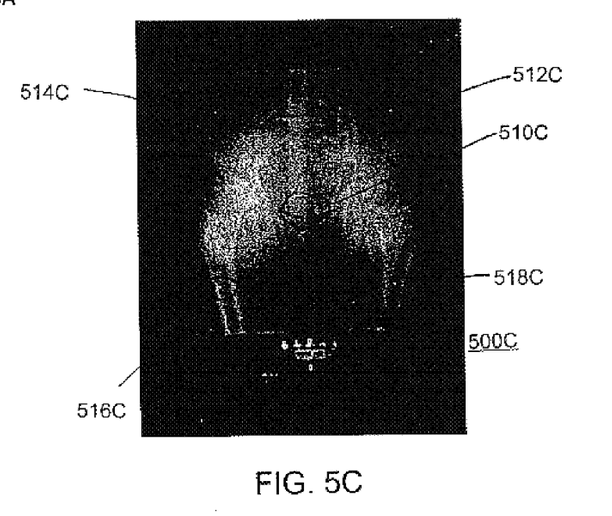

FIG. 5C shows the image 500C of FIG. 5A after the image has been flipped stereoscopically according to the present invention. In FIG. 5C, the graphics engine 130 adjusted the screen parallax to bring the corner pointers 512C, 514C, 516C, 518C to the level of the screen, preferably by making the respective corner pointers on the left and right images coincide. The middle pointer 510C, in contrast, is now located behind the screen. Accordingly, the flipped image can easily be viewed by a radiologist.

The above description is included to illustrate the operation of the preferred embodiments and is not meant to limit the scope of the invention. The scope of the invention is to be limited only by the following claims. From the above discussion, many variations will be apparent to one skilled in the relevant art that would yet be encompassed by the spirit and scope of the invention.

What is claimed is:

1. A method for manipulating a stereoscopic radiograph comprised of first and second images generated by a radiographic system, wherein the first and second images include images of physical pointers, the method comprising the steps of:

defining a first screen parallax for the stereoscopic radiograph, the first screen parallax defining a first 3-Dimensional (3-D) perspective of the stereoscopic radiograph;

flipping the first and second images about a vertical axis to produce a second stereoscopic radiograph having a second screen parallax, the second screen parallax defining a second 3-D perspective of the second stereoscopic radiograph; and modifying the second screen parallax to produce a third 3-D perspective of the second stereoscopic radiograph and to place selected ones of the physical pointers at a predetermined depth in the third 3-D perspective of the stereoscopic radiograph.

2. The method of claim 1, wherein the third 3-D perspective is equivalent to viewing the stereoscopic radiograph having the first 3-D perspective from behind.

3. The method of claim 1, further comprising the step of: determining a geometry of the radiographic system; wherein the modifying step modifies the second screen parallax responsive to the determined geometry.

4. The method of claim 3, wherein the determining step comprises the substep of:

recovering the geometry of the radiographic system from the first and second images.

5. The method of claim 1, wherein the predetermined depth is at a level of a display screen.

6. The method of claim 1, further comprising the step of: converting the first and second images to a parallel geometry to reduce depth curvature distortion in the stereoscopic radiograph.

7. The method of claim 1, further comprising the step of: processing the first and second images to account for keystone distortion in the stereoscopic radiograph.

8. A computer-readable medium comprising:

a computer program product having computer-readable code embodied therein for manipulating a stereoscopic radiograph comprised of first and second images generated by a radiographic system, wherein the first and second images include images of physical pointers, the computer program product comprising:

a module for defining a first screen parallax for the stereoscopic radiograph, the first screen parallax defining a first 3-Dimensional (3-D) perspective of the stereoscopic radiograph;

a module for flipping the first and second images about a vertical axis to produce a second stereoscopic radiograph having a second screen parallax, the second screen parallax defining a second 3-D perspective of the second stereoscopic radiograph; and a module for modifying the second screen parallax to produce a third 3-D perspective of the second stereoscopic radiograph and to place selected ones of the pointers at a predetermined depth in the third 3-D perspective of the stereoscopic radiograph.

9. The computer-readable medium of claim 8, wherein the third 3-D perspective is equivalent to viewing the stereoscopic radiograph having the first 3-D perspective from behind.

10. The computer-readable medium of claim 8, further comprising:

a module for determining a geometry of the radiographic system;

wherein the module for modifying the second screen parallax modifies the second screen parallax responsive to the determined geometry.

11. The computer-readable medium of claim 10, wherein the module for determining the geometry of the radiographic system comprises:

a module for recovering the geometry of the radiographic system from the first and second images.

12. The computer-readable medium of claim 8, wherein the predetermined depth is at a level of a display screen.

13. The computer-readable medium of claim 8, wherein the computer program product further comprises:

a module for converting the first and second images to a parallel geometry to reduce depth curvature distortion in the stereoscopic radiograph.

14. The computer-readable medium of claim 8, wherein the computer program product further comprises:

a module for processing the first and second images to account for keystone distortion in the stereoscopic radiograph.

15. A graphics engine for manipulating a stereoscopic radiograph comprised of first and second images generated by a radiographic system, wherein the first and second images include images of physical pointers, the graphics engine comprising:

a module for defining a first screen parallax for the stereoscopic radiograph, the first screen parallax defining a first 3-Dimensional (3-D) perspective of the stereoscopic radiograph;

a module for flipping the first and second images about a vertical axis to produce a second stereoscopic radiograph having a second screen parallax, the second screen parallax defining a second 3-D perspective of the second stereoscopic radiograph; and a module for modifying the second screen parallax to produce a third 3-D perspective of the second stereoscopic radiograph and to place selected ones of the physical pointers at a predetermined depth in the third 3-D perspective of the stereoscopic radiograph.

16. The graphics engine of claim 15, wherein the third 3-D perspective is equivalent to viewing the stereoscopic radiograph having the first 3-D perspective from behind.

17. The graphics engine of claim 15, further comprising:

a module for determining a geometry of the radiographic system;

wherein the module for modifying the second screen parallax modifies the second screen parallax responsive to the determined geometry.

18. The graphics engine of claim 17, wherein the module for determining the geometry of the radiographic system comprises:

a module for recovering the geometry of the radiographic system from the first and second images.

19. The graphics engine of claim 15, wherein the predetermined depth is at a level of a display screen.

20. The graphics engine of claim 15, further comprising:

a module for converting the first and second images to a parallel geometry to reduce depth curvature distortion in the stereoscopic radiograph.

21. The graphics engine of claim 15, further comprising:

a module for processing the first and second images to account for keystone distortion in the stereoscopic radiograph.

* * * * *